United States Patent [19]

Otto

[11] 4,048,016

[45] Sept. 13, 1977

[54] IDENTIFICATION OF NON-FERMENTATIVE GRAM-NEGATIVE BACTERIA

[75] Inventor: Lucy A. Otto, Garden Grove, Calif.

[73] Assignee: The United States of America as represented by the Department of Health, Education and Welfare, Washington, D.C.

[21] Appl. No.: 571,502

[22] Filed: Apr. 25, 1975

[51] Int. Cl.$^2$ ............................ C12K 1/10; C12K 1/00
[52] U.S. Cl. ............................ 195/100; 195/103.5 M; 195/139
[58] Field of Search ................ 195/103.5 R, 100, 139, 195/103.5 M

[56] References Cited

U.S. PATENT DOCUMENTS 3,632,478   1/1972   Fink ............................ 195/103.5 R

OTHER PUBLICATIONS

Otto et al., "Gram-Negative Nonfermentative Bacilli:Identification by a Nutritional Agar Method" presented before the American Soc. for Microbiology, Chicago, Illinois, on May 17, 1974.

Pickett et al., "Characterization of Saccharolytic Nonfermentative Bacteria Associated with Man", Can. J. Microbiol, vol. 16, pp. 351-362 (1970).

Pickett et al., "Salient Features of Nonsaccharolytic & Weakly Saccharolytic Nonfermentative Rods", Can. J. Microbiol, vol. 16, No. 6, pp. 401-409 (1970).

Hugh et al., "The Taxonomic Significance of Fermentative Versus Oxidative Metabolism of Carbohydrates by Various Gram Negative Bacteria", J. Bacteriol, vol. 66, pp. 24-26 (1953).

Stanier et al., "The Aerobic Pseudomonads : A Taxonomic Study", J. Gen. Microbiol, vol. 43, pp. 159-217 (1966).

*Primary Examiner*—David M. Naff
*Assistant Examiner*—C. A. Fan
*Attorney, Agent, or Firm*—John S. Roberts, Jr.; Norman J. Latker; Thomas G. Ferris

[57] ABSTRACT

A method for identification of non-fermentative Gram-negative bacteria (NFB) consisting of correlating results from a plurality of oxidative alkalinization (OAL) assays in media samples consisting essentially of a minimal-protein medium, an indicator and a substrate and a plurality of oxidative acidification (OAC) assays in media consisting essentially of a minimal-protein medium, an indicator and a substrate. A medium for determining oxidative attack (OA) consists essentially of a minimal-protein medium, an indicator and a substrate.

9 Claims, No Drawings

IDENTIFICATION OF NON-FERMENTATIVE GRAM-NEGATIVE BACTERIA

Although techniques for the rapid identification of pathogens such as the Enterobacteriaceae, which cause diseases of which typhoid and cholera are typical, are well developed, tests for these organisms frequently depend upon their anaerobic or fermentative reactions and, consequently, are useless for the identification of Gram-negative non-fermentative organisms, such as the Pseudomonadaceae, Azotobacteraceae, Rhizobiaceace, Methylomonodaceae, and Halobacteriaceae families and unaffiliated genera including Alcaligenes, Acetobacter, Brucella, Bordetella, Francisella and Thermus.

Although the Gram-negative non-fermentative bacteria (NFB) are less active biochemically than enteric pathogens, the NFB are widely distributed in soil, water, milk, cosmetics and disinfectants. The NFB are generally less virulent than Enterobacteriaceae or the like and act as opportunistic invaders, rather than as pathogens. However, NFB organisms can cause mild to severe, or even fatal, disease in host organisms debilitated by traumatic injury, e.g., surgery or burns, immuno-suppressant drugs or prior infection with a strong pathogen.

Because of their relative biochemical inactivity, the NFB organisms cannot be identified using the oxidative/fermentative medium (O/F) used since about 1953, according to Hugh and Leifson, for discerning whether attack upon a carbohydrate substrate by an organism is oxidative. Among other reasons, the O/F medium is unsuitable for assay of NFB because it contains large amounts of peptone, a protein, which acts as a buffer itself or in the form of degradation products so that small amounts of acid from aerobic (nonfermentative) oxidation are not detectable at all or are detectable only after several days, up to as many as six to ten days, of incubation. It is apparent that this lengthy period of incubation, coupled with the unreliable results obtained, makes the O/F medium unacceptable for rapid reliable assay of NFB isolated from clinical specimens or from other sources.

Other assay methods used to identify NFB include a buffered single substrate (BSS) and assimilation. The BSS method, according to M. J. Pickett et al., "Characterization of saccharolytic non-fermentative bacteria associated with man," *Can. J. Microbiol.*, Vol. 16, 351–362 (1970) and M. J. Pickett et al., "Salient features of nonsaccharolytic and weakly saccharolytic non-fermentative rods," *Can. J. Microbiol.*, Vol. 16, 401–409 (1970), uses as medium 0.5% sodium chloride, 0.1% agar, 0.002% phenol red, and 0.0002% crystal violet in 0.02 molar potassium phosphate at pH 6.5. Most of the substrates in the Pickett testing were used in concentrations of 0.5%. However, the BSS method requires incubation periods of 4 to 6 days and is, therefore, tedious. Moreover, weak reactions are difficult to read in the BSS method, which is usable for all types of substrates.

The assimilation method [R. Y. Stanier et al., "The aerobic pseudomonads: a taxonomic study," *J. Gen. Microbiol.*, Vol. 43, 159–217 (1966)] was as a basic medium material prepared from a standard mineral base containing phosphate buffer (1 molar; pH 6.8), Hutner's vitamin-free mineral base and 1.0 gram of sodium sulfate per liter. The basal medium is heavily chelated with nitrilotriacetic acid and ethylenediamine tetraacetic acid. The mineral base is mixed with yeast extract medium (5 grams of yeast extract per liter) or yeast agar medium (5 grams of yeast extract and 20 grams of agar per liter). The substrate being assayed is used in the amount of 1–3 grams per liter, added to the above medium, solidified by the addition of 1 % of Ionagar. However, the Stanier method is suitable only for a research laboratory, because the method requires extended incubation and large amounts of media, as well as supplementation for "fastidious" organisms. Moreover, the method is difficult to read because a nonstandard inoculum is used in a replica plating technique.

Kits available on the market, such as the API kit or Auxotab, are totally inappropriate for the assay of NFB, because these kits depend on fermentative reactions for reliable readings.

It will be understood that, in a clinical situation, speedy and accurate identification of organisms isolated from patients is always of paramount importance. In regard to identification of specimens from debilitated patients suspected of being infected with an NFB infection, the requirement of rapid and reliable assay methods has not heretofore been met. Thus, as to the NFB organisms, there is a long-felt need for an assay medium and an assay method which is simple, sensitive, reliable and fast, especially for fastidious organisms. Additionally, an assay for NFB should be economical both in initial cost and in material, incubator space, storage space and analytical time.

It has been found, in accordance with this invention that a medium for rapidly and accurately determining oxidative attack (OA) by NFB consists of a minimal protein medium, an indicator and a substrate. It has further been found that, if an oxidative acidification (AOC) assay is required, the substrate is selected from among polyalcohols, pentoses, hexoses, disaccharides and ketoses. When an oxidative alkalinization assay is required, the substrate may be selected from among phenylalanine, acetamide, nicotinamide, glutamine, allantoin, asparagine, and malonate, citrate, tartrate and saccharate salts.

"Minimal-protein," as used in the specification and claims to apply to a medium for OAL or OAC assays, means a medium which contains from about 0.02 to about 0.05% by weight of a protein or protein degradation products per liter of solution. For the purposes of the OAL assays, the preferred protein is casamino acids, present in the range from about 0.02 to about 0.05%, preferably between about 0.04% and 0.05% by weight. For the OAC assays, the preferred protein is tryptone, in the range from about 0.02 to about 0.03% by weight. Preferably, the amount of tryptone is about 0.2 grams per liter.

It has further been found, in accordance with this invention, that a method for identifying NFB consists of correlating results from a plurality of OAL assays and a plurality of OAC assays. Preferably, the OAL assays and the OAC assays are carried out in separate compartmented trays, each compartment of which contains minimal protein medium, bromthymol blue indicator and a different substrate, the OAL substrates being assayed in one tray and the OAC substrates in a second compartmented tray.

"A plurality of assays," as used herein, means several assays. It will be appreciated that the particular assays to be performed will be selected by the worker in accordance with knowledge of the organisms suspected to be present in the culture and that arbitrary limitations of the number of assays to be performed cannot be made. See Stanier, above, at 170–171, for a listing of substrates tested for aerobic oxidation by NFB. However, it preferably includes among the OAC asays a test for each of polyalcohols, pentoses, disaccharides and ketoses; and among OAL assays a test for each of dicarboxylic acids, tricarboxylic acids, hydroxy acids, sugar derivatives, ring amino acids, amides, amines and miscellaneous nitrogen compounds. It will also be understood tha the reliability of identification of an organism increases as the number of assays is increased.

Most preferably, the OAC assays will include those for glycerol, M-inositol, D-mannitol, cellobiose, lactose, L-arabinose, D-ribose, D-xylose, rhamnose, and D-fructose, whereas the OAL assays will include all of the following: phenylalanine, acetamide, nicotinamide, glutamine, allantoin, asparagine, and malonate, citrate, tartrate and saccharate salts.

It has been found, in accordance with this invention, that the media and method of my invention provides an accurate, simple, reliable and economical way of assaying NFB obtained from clinical specimens or otherwise. It has been found that the OAC testing is accurate for genera Pseudomonas, Acinetobacter, Flavobacterium, Moraxella and Xanthomonas, as being typical of the Gram-negative aerobic rods and cocci (NFB) classified according to "Bergey's Manual of Determinative Bacteriology," Williams and Wilkins Company, Baltimore, 8th ed. (1974). It has been found that OAL testing is accurate for genera Pseudomonas, Acinetobacter, Alcaligenes, Bordetella, Flavobacterium, Moraxella and Xanthomonas, as being exemplary of NFB.

A medium found suitable for OAL in accordance with this invention includes sodium sulfate (2 grams/liter), magnesium sulfate heptahydrate (0.1 gram/liter), calcium chloride dihydrate (0.1 milligram/liter), mineral salts (trace), bromthymol blue (80 milligrams/liter), yeast extract (0.5 gram/liter) and casamino acids (0.5 gram/liter) and distilled water, using phosphate buffer (0.00125 molar) to obtain a final pH of 6.0.

Substrates used for OAL according to this invention include salts of dicarboxylic acids, such as malonates; tricarboxylic acids, e.g., citrate; hydroxy acids, e.g., tartrate; sugar derivatives, e.g., saccharates; ring amino acids, e.g., phenylalanine; amides, such as acetamide and nicotamide; amines such as glutamine; and miscellaneous nitrogen compounds, such as allantoin and asparagine at a level of about 0.2%.

The test system of choice is an air-tight, autoclavable, compartmented box, each compartment of which contains a single substrate in 0.7 milliliter of basic medium. Division of the box into compartments prevents cross-feeding and/or masking of a weak reaction by a strong reaction, as is a problem with the assimilation technique. Incubation is carried at 30° C. for a maximum of 3 days. Reactions are interpreted as follows: dark blue — strongly positive; green — weakly positive; yellow-green — negative.

A medium found suitable for OAC in accordance with this invention consists of tryptone (0.2 gram/liter), sodium chloride (0.5 gram/liter), bromthymol blue (0.08 gram/liter), ion agar (8.5 grams/liter) and distilled water, buffered with phosphate buffer (0.0007 molar) to a pH of 6.7.

Substrates used for OAC in accordance with this invention include polyalcohols, such as glycerol, M-inositol, and D-mannitol; disaccharides such as a cellobiose and lactose; pentoses including L-arabinose, D-ribose, D-xylose and rhamnose; ketoses such as D-fructose; and hexoses such as glucose at a level of about 2%.

As for the OAL test, the preferred test system is an air-tight, autoclavable, compartmented box, each compartment of which contains a single substrate in 0.7 milliliter of basic medium. Incubation is carried out at 30° C. for a maximum of 3 days. Reactions are interpreted as follows: bright yellow— strongly positive; green — weakly positive; dark blue — negative.

A kit for the identification of NFB organisms consists of a compartmented tray containing media for OAL assays and a compartmented tray for OAC assays, wherein each compartment contains minimal protein medium, an indicator and a different substrate. Preferably, the indicator in each case is bromthymol blue and substrates for the OAL assays are selected from the group consisting of phenylalanine, acetamide, nicotinamide, glutamine, allantoin, asparagine and malonate, citrate, tartrate and saccharate salts and substrates for the OAC assays are selected from the group consisting of glycerol, M-inositol, D-mannitol, L-arabinose, D-ribose, D-xylose, rhamnose, cellobiose, lactose and D-fructose.

The following examples are presented as typical of the practice of this invention.

EXAMPLE 1

Oxidative acidification medium (OAC) was made as above and evaluated against oxidative/fermentation medium (O/F) by incubation at 30° C. Results were determined by color change of the indicator for 17 strains of four species of Pseudomonas. These NFB were obtained from the Communicable Disease Center, Atlanta, Georgia, from the collection at the Food and Drug Administration, Los Angeles, California, and from M. J. Pickett.

Open tubes were used for the O/F studies. These samples wer incubated for seven days.

The OAC tests were performed in an air-tight, compartmented autoclave box (Bionics Corp., Carson, Colorado), each compartment of which contained a single substrate in 0.7 milliliter of basal medium. A single drop of culture from a Pasteur Pipette (about $10^{11}$ organisms per milliliter) was dropped on the agar surface of each compartment and was also used to inoculate the O/F medium. Daily readings were made, for a maximum of three days with the OAC system and for a maximum of seven days for the O/F system in a comparison test which follows as Table I.

Table 1.

| | Comparison of OAC vs. O/F Reactions of Weakly Saccharolytic Pseudomonads | | | | | | | |
|---|---|---|---|---|---|---|---|---|
| | Pseudomonas | | | | | | | |
| No. of Strains | vesiculare 3 | | acidovorans 3 | | maltophilia 7 | | pseudo-alcaligenes 4 | |
| | OAC | O/F | OAC | O/F | OAC | O/F | OAC | O/F |
| L-Arabinose | $v^2$ | — | — | — | v | — | — | — |
| Cellobiose | + | — | — | — | v | $v_w^3$ | — | — |
| D-Fructose | — | — | v | $+^4$ | + | $v_w^3$ | + | + |

Table 1.-continued

Comparison of OAC vs. O/F Reactions of Weakly Saccharolytic Pseudomonads

| No. of Strains | Pseudomonas | | | | | | | |
|---|---|---|---|---|---|---|---|---|
| | vesiculare 3 | | acidovorans 3 | | maltophilia 7 | | pseudo-alcaligenes 4 | |
| | OAC | O/F | OAC | O/F | OAC | O/F | OAC | O/F |
| D-Galactose | + | +$_w$ | − | v$^4$ | +$^3$ | v$_w^2$ | − | − |
| D-Glucose | + | +$_w$ | − | − | +$^{2-3}$ | v$^2$ | − | − |
| Glycerol | − | − | v | v$^4$ | − | − | v | v$_w^4$ |
| m-Inositol | − | − | − | v$^4$ | − | − | − | − |
| Lactose | − | − | − | − | v | v$_w^3$ | − | − |
| Maltose | + | v$_w^2$ | − | − | + | +$_w^2$ | − | − |
| D-Mannitol | − | − | + | +$^4$ | − | − | − | v |
| D-Mannose | − | − | − | − | + | v$_w^2$ | − | − |
| Melibiose | − | − | − | − | v$_w^2$ | v$_w^2$ | − | − |
| Rhamnose | − | − | − | − | − | − | − | − |
| D-Ribose | − | − | − | − | − | − | − | − |
| Sorbitol | − | − | − | − | − | − | − | − |
| Sucrose | − | − | − | − | v$_w^2$ | − | − | − |
| D-Trehalose | − | − | − | − | − | ND | − | − |
| D-Xylose | v | − | v | − | v$_w^2$ | − | − | − |

OAC=Oxidative Acidification Basal Medium; O/F = O/F Basal medium; + = 80% or more positive; − = 0 to 19% positive; V=20-80% positive. ND=not done. Superscripts show days of incubation before first positive reaction appeared. Subscript "w" indicates a weak positive reaction. No superscript indicates that positive reactions appeared within 1 day of incubation.

From the data presented in Table I, it will be appreciated that the OAC medium, used in accordance with this invention, consistently gave more rapid, stronger, and less ambiguous test results than the O/F medium plus substrate.

EXAMPLE 2

Pseudomonas strains, obtained from the Communicable Disease Center, Atlanta, Georgia, and from the collection at the Food and Drug Administration, Los Angeles, California, were used for the evaluation of the oxidative alkalinization media (OAL) described above. The tests were compared with the BSS method [M. J. Pickett et al., "Nonfermentative Bacilli associated with man," Am. J. Clin. Path., Vol. 54, 164–177 (1970)]. Results are given in Table II.

Table 2.

Comparison of OAL vs. BSS$^a$ reactions.

| No. Strains | Pseudomonas | | | | | | | |
|---|---|---|---|---|---|---|---|---|
| | acidovorans 3 | | maltophilia 7 | | pseudo-alcaligenes 4 | | stutzeri 5 | |
| | OAL$^b$ | BSS | OAL | BSS | OAL | BSS | OAL | BSS |
| Butyrate | + | − | + | +$_w^3$ | v$^{1-3}$ | v$^3$ | +$^2$ | − |
| p-OHBenzoate | + | − | − | − | − | − | − | − |
| Citrate | + | + | + | + | + | + | + | + |
| Lactate | + | − | + | + | + | + | + | + |
| Malonate | + | +$^2$ | v | v | − | − | + | + |
| Nicotinate | + | − | − | − | − | − | v | v |
| Propionate | +$^2$ | − | + | +$^{1-3}$ | − | v$_w^4$ | v | v |
| B-Alanine | +$_w$ | − | − | − | + | v$_w^3$ | v | v |
| Betaine | − | − | − | − | +$^{1-3}$ | v$_w^4$ | − | − |
| Serine | − | − | + | + | + | +$^3$ | + | v |
| Allantoin | + | − | − | − | + | − | v | v |

$^a$BSS, buffered single substrate; other abbreviations and notations as for Table 1.
$^b$OAL, oxidative alkalinization medium.

From the data presented in Table II, it will be seen that the OAL medium, used in accordance with this invention, gives more rapid and less ambiguous results than the BSS method.

EXAMPLE 3

The reliability of the OA system was evaluated on salts (the OAL test) and on carbohydrates (the OAC system) using representative organisms from genera Pseudomonas, Acinetobacter, and Flavobacterium. Results are shown in Table III.

TABLE 3.

Reproducibility of the OA System.

| Organisms | Strain No. | "Salts"*$^a$ | |
|---|---|---|---|
| | | No. Runs | Variation |
| P. putida | 5 | 7 | none |
| P. fluorescens | 6 | 7 | 1 (tar +) |
| P. aeruginosa | 128 | 11 | none |
| A. anitratus | 133 | 11 | none |
| F. meningosepticum | 26 | 7 | 1 (φ Ala +$_w^2$) |
| P. pseudoalcaligenes | 92 | 6 | 3 (2 nic, φ ala +) |
| P. stutzeri | 123 | 2 | none |
| P. maltophilia | 122 | 2 | none |
| A. lwoffii | 44 | 2 | none |
| | | 55 | 5 |

| Organisms | Strain No. | Carbohydrates* | |
|---|---|---|---|
| | | No. Runs | Variation |
| P. putida | 5 | 11 | 1 (lac −) |
| P. fluorescens | 6 | 11 | none |
| P. aeruginosa | 128 | 7 | 1 (cel −) |
| A. anitratus | 133 | 6 | 2 (mannitol +) |
| F. menigosepticum | 26 | 7 | 3 (2 ara +, lac −) |
| P. pseudoalcaligenes | 92 | 6 | none |
| | | 48 | 7 |

*10 substrates each.
$^a$"Salts" include the substrates which produce an alkaline reaction when degraded Thus, it is apparent that reproducibility using either the OAC medium or the OAl medium is very high.

EXAMPLE 4

Stability studies of the OA media were performed by preparing and autoclaving boxes filled according to the OAC or OAL protocols of Examples 1, 2 or 3 and storing the media at 5°-7° C. in sealed plastic bags. Samples were made in this way, incorporating ten carbohydrates for the OAC test (arabinose, cellobiose, fructose, inositol, lactose, mannitol, rhamnose, ribose, xylose and glycerol) and of ten "salts" for the OAL test (acetamide, allantoin, asparagine, glutamine, nicotinamide, citrate, malonate, saccharate, tartrate and phenylalanine). The OAC media were assayed weekly for 6 weeks with single straings of *P. putida* and *F. meningosepticum*. The OAL media were assayed intermittently for 2 months with 15 strains of the following organisms: *P. aeruginose, P. putida, P. stutzeri, P. fluorescens, P. maltophilia, A. anitratus* and *A. lwoffi.*

No variation in test results was found over the 6 weeks' testing regimen. Because the organisms were selected to include those which attacked the various substrates strongly or weakly, it is thought that the OA media prepared according to this invention has relatively high stability under the indicated storage conditions.

EXAMPLE 5

The following is a recommended protocol for speciating NFB: determinig oxidase activity from cells from a triple sugar iron agar (TSI) or Kligler's Iron Agar (KIA) slant, inoculating motility nitrate, FLN medium and Brucella broth (for incubation at 42° C.) and making a heavy suspension with 0.5 - 1.0 milliliter of sterile distilled water. The suspension is used to inoculate OA substrates, lysine decarboxylase (LDC), indole and gluconate media.

When growth is light, e.g., Moraxellae and other fastidious species, the entire surface of a large Brucella slant (25 millimeter tube containing 10 milliliters of medium, slanted so that there is no butt) is inoculated and incubated for 24 hours at 30° C. Pigment sensitivity is determined only if the isolate is non-pigmented, oxidase positive, and non-motile. Typical results are given in Table IV.

Table 4

Saccharolytic NFB - Recommended Tests

| Primary Tests | P. aeruginosa | P. fluorescence | P. putida | P. cepacea | P. pickettii | P. stutzeri | Xanthomonas | A. anitratus | CDC V-A | CDC IIk |
|---|---|---|---|---|---|---|---|---|---|---|
| Pigment | (+) | − | − | − | − | − | + | − | − | − |
| Oxidase | + | + | + | + | + | + | + | − | + | + |
| Motility | + | + | + | + | + | + | + | − | + | + |
| Nitrite | + | − | − | − | + | + | − | − | − | − |
| N₂ Production | + | − | − | + | + | + | − | − | − | − |
| Fluorescence | + | + | + | − | − | − | − | − | − | − |
| 42° C. | + | − | − | + | − | + | − | + | + | + |
| Penicillin Sens. | − | − | − | − | − | − | (+) | + | − | − |
| Indol | − | − | − | − | − | − | − | − | − | − |
| Gluconate | > | + | + | − | − | − | − | − | − | − |
| LDC | − | − | − | + | − | − | − | − | − | − |
| "Salts" | − | − | − | + | − | − | − | − | − | − |
| Acetamide | + | − | − | + | − | + | − | − | − | + |
| Allantoin | +² | +² | +² | > | > | > | − | > | + | > |
| Malonate | + | + | + | + | + | + | − | + | + | > |
| Propionate | − | +² | +² | + | + | > | − | + | + | > |
| Saccharate | + | +² | +² | + | + | +² | − | + | +² | > |
| Tartrate | − | + | − | + | + | > | +² | + | > | > |
| Serine | + | + | + | + | > | > | − | > | > | > |
| B-Alanine | − | − | − | + | + | − | − | − | − | − |
| Carbohydrates | | | | | | | | | | |
| Arabinose | + | + | + | + | + | + | + | + | + | + |
| Cellobiose | − | + | − | + | + | − | + | + | + | + |
| Fructose | + | + | + | + | + | + | + | − | + | + |
| Lactose | − | + | − | + | > | > | + | − | + | + |
| Maltose | − | − | − | + | − | > | + | +³ | > | > |
| Mannitol | + | + | − | + | + | > | − | − | − | > |

Non-Saccharolytic and Weakly Saccharolytic NFB - Recommended Tests

| Tests | P. acidovorans | P. pseudo-alcaligenes | P. malto-philia | P. vesi-culare | P. dimi-nuta | P. alca-ligenes | A. dentri-ficans | A. fae-calis | A. od-orans | B. bronch-iseptica | A. lwoffi | Flavobacterium I | Flavobacterium IIb | Flavobacterium III | M. nonli-quefaciens | M. oslo-ensis | M. phenyl pyruvica |
|---|---|---|---|---|---|---|---|---|---|---|---|---|---|---|---|---|---|
| Pigment | − | − | − | (+) | + | − | − | − | − | − | − | − | − | − | − | − | − |
| Oxidase | + | + | − | − | (+) | + | + | + | + | + | − | + | + | + | + | + | + |
| Motility | + | + | + | − | + | + | + | + | + | + | − | − | − | − | − | − | (+) |
| Nitrite Production | + | + | + | (+) | − | − | + | + | − | − | − | − | − | − | − | − | − |
| N₂ Production | − | − | − | − | − | − | + | − | − | − | − | − | − | − | − | − | − |
| Fluorescence | − | − | − | − | − | − | − | − | − | − | − | − | − | − | − | − | − |
| 42° C. | − | + | + | − | − | − | + | + | + | + | − | − | − | − | + | − | − |
| Penicillin sens. | − | − | − | − | − | − | − | − | − | − | + | + | + | + | + | + | + |
| Indol | − | − | − | − | − | − | − | − | − | − | − | − | − | + | − | − | − |
| Gluconate | − | − | − | + | − | − | − | − | − | − | + | − | − | − | − | − | − |
| LDC Salts | − | − | − | − | − | − | − | − | − | − | + | − | − | − | − | − | − |
| Acetamide | + | +² | −² | − | − | − | − | +² | +² | − | − | − | − | − | − | − | − |
| Allantoin | + | + | v² | − | − | − | − | + | > | − | + | − | − | − | − | − | − |
| Malonate | + | + | − | − | − | − | − | + | + | + | + | − | − | + | − | − | − |

Table 4-continued

| | | | | | | | | | | | | | | | | | |
|---|---|---|---|---|---|---|---|---|---|---|---|---|---|---|---|---|---|
| Propionate | +² | | | | | | | + | | + | | | | | | | + |
| Saccharate | + | | | | + | + | | + | + | ND | | | | | | | |
| Tartrate | + | + | | | +++ | ++ | | +> | >ND | v² | +  | +  | | | | v² | v²⁻³ | |
| Serine | + | + | | | | | | | | | | | | | | | | |
| B-Alanine | | | | | | | | | | | | | | | | | | |
| Carbohydrates | | | | | | | | | | | | | | | | | | |
| Arabinose | | | >>+>+ | v²+ +  | | | | | | | | | | | | | | |
| Cellobiose | | + | | | | | | | | | | | | | | | | |
| Fructose | > | | | | | | | | | | | | +  | | | | | |
| Lactose | | | | | | | | | | | | | | | | | | |
| Maltose | | | | | | | | | | | | +  | | | | | | |
| Mannitol | + | | | | | | | | | | | | | | | | | |

From the foregoing data, it is apparent that 92% of the strains studied, except Moraxella, could be identified after 24 hours' incubation.

EXAMPLE 6

A one-piece kit is constructed so that the air space above each compartment is physically separated from the air space above every other compartment. The OAL and OAC media are then put in each of the compartments and the assay is done as in the foregoing examples.

It will be appreciated that, when the air spaces above each of the compartments are physically separated in this manner, the possibility of obtaining false positive results is greatly reduced, even when both OAL and OAC tests are being carried out in the same kit.

Reference is made to a paper presented by Lucy A. Otto and M. J. Pickett, "Gram-Negative Nonfermentative Bacilli: Identification by a Nutritional Agar Method," presented before the American Society for Microbiology, Chicago, Illinois, on May 17, 1974. This paper is incorporated herein by reference.

What is claimed is:

1. Assay medium for determining oxidative attack (OA) by Gram-negative non-fermentative bacteria (NFB) consisting essentially of an oxidative alkalination (OAL) assay medium containing 0.02 –0.05% by weight of casamino acids, bromthymol blue indicator, a substrate and buffered to pH 6.0 and an oxidative acidification (OAC) medium containing 0.02–0.03% by weight of tryptone, bromthymol blue indicator, a substrate and buffered to pH 6.7.

2. The medium of claim 1, wherein the substrate for the OAL medium is selected from the group consisting of phenylalanine, acetamide, nicotinamide, glutamine, allantoin, asparagine and malonate, citrate, tartrate and saccharate salts.

3. The medium of claim 1, wherein the substrate for the OAC medium is selected from the group consisting of polyalcohols, pentoses, disaccharides, ketoses, and hexoses.

4. A method for the identification of "an unknown" non-fermentative Gram-negative bacteria (NFB) consisting of testing said unknown by the results of a battery of oxidative alkalination (OAL) assays in media samples consisting essentially of a minimal-protein medium containing 0.02-0.05% by weight of casamino acids and buffered to pH 6.0, bromthymol blue indicator and a substrate and a plurality of oxidative acidification (OAC) assays in media samples consisting essentially of a minimal-protein medium containing 0.02-0.03% by weight of tryptone and buffered to pH 6.7, bromthymol blue indicator and a substrate.

5. The method of claim 4, wherein the OAC and OAL assays are carried out in separate compartmented trays, each compartment of which contains minimal-protein medium, bromthymol blue indicator and a different substrate, the OAL substrates being assayed in one tray and the OAC substrates in a second compartmented tray.

6. The method of claim 4, wherein the substrate for the OAC assays is selected from the group consisting of polyalcohols, pentoses, disaccharides and ketoses and the polyalcohols are glycerol, M-inositol, or D-mannitol; the pentoses are L-arabinose, D-ribose, D-xylose or rhamnose; the disaccharides are cellobiose or lactose; and the ketose is D-fructose; wherein the substrate for the OAL assays is selected from the group consisting of phenylalanine, acetamide, nicotinamide, glutamine, allantoin, asparagine and malonate, citrate, tartrate and saccharate salts.

7. The method of claim 6, wherein the OAL substrates are assayed in one compartmented tray, each compartment of which contains minimal-protein medium, bromthymol blue indicator and substrate; and wherein the OAC substrates are assayed in a second compartmented tray, each compartment of which contains minimal-protein medium, bromthymol blue indicator and substrate.

8. A kit for the identification of non-fermentative Gram-negative bacteria (NFB) consisting of a compartmented tray containing media for oxidative alkalination (OAL) assays and a compartmented tray containing media for oxidative acidification (OAC) assays, wherein each compartment contains minimal-protein medium, bromthymol blue indicator and a different substrate, and wherein minimal-protein media for OAL assays contains 0.02-0.05% by weight of casamino acids and is buffered to pH 6.0 and for OAC asays contains 0.02-0.03% by weight of tryptone and is buffered to pH 6.7.

9. The kit of claim 8, wherein the compartmented tray for OAL assays contains separate compartments, each of which contains minimal-protein medium, bromthymol blue indicator and a substrate selected from the group consisting of phenylalanine, acetamide, nicotinamide, glutamine, allantoin, asparagine, and malonate, citrate, tartrate and saccharate salts; and wherein the compartmented tray for OAC assays contains separate compartments, each of which contains minimal-protein medium, bromthymol blue indicator and a substrate selected from the group consisting of glycerol, M-inositol, D-mannitol, L-arabinose, D-ribose, D-xylose, rhamnose, cellobiose, lactose and D-fructose.

* * * * *